(12) United States Patent
O'Connell

(10) Patent No.: US 6,235,011 B1
(45) Date of Patent: May 22, 2001

(54) THREE-PIECE TAPE LANDING ZONE FOR DIAPERS

(75) Inventor: Susan L. O'Connell, Dunwoody, GA (US)

(73) Assignee: Paragon Trade Brands, Inc., Norcross, GA (US)

(*) Notice: Subject to any disclaimer, the term of this patent is extended or adjusted under 35 U.S.C. 154(b) by 0 days.

(21) Appl. No.: 09/076,096

(22) Filed: May 12, 1998

Related U.S. Application Data

(60) Provisional application No. 60/048,185, filed on May 30, 1997.

(51) Int. Cl.[7] .................................................. A61F 13/15
(52) U.S. Cl. .................. 604/390; 604/372; 604/378; 604/385.27; 604/385.28
(58) Field of Search .................................. 604/372, 378, 604/385.1–387, 389–391, 385.01, 385.03, 385.27, 385.28

(56) References Cited

U.S. PATENT DOCUMENTS

| | | | |
|---|---|---|---|
| 5,024,672 | * | 6/1991 | Widlund .............................. 604/396 |
| 5,026,446 | * | 6/1991 | Johnston et al. ..................... 604/389 |
| 5,275,590 | | 1/1994 | Huffman et al. ................... 604/385.2 |
| 5,527,305 | * | 6/1996 | Goulait et al. ....................... 604/390 |
| 5,599,620 | * | 2/1997 | Huskey . |
| 5,738,930 | * | 4/1998 | Huskey . |

FOREIGN PATENT DOCUMENTS

| | | | |
|---|---|---|---|
| 2021538 | | 1/1992 | (CA) . |
| 0 532 805 | * | 3/1993 | (EP) ..................................... 604/389 |
| 2 277 865 | * | 11/1994 | (GB) ..................................... 604/390 |
| 2 277 866 | * | 11/1994 | (GB) ..................................... 604/390 |

OTHER PUBLICATIONS

International Search Report for PCT/US98/10727.

* cited by examiner

*Primary Examiner*—Glenn K. Dawson
*Assistant Examiner*—K. M. Reichle
(74) *Attorney, Agent, or Firm*—Hunton & Williams

(57) ABSTRACT

A three-piece tape landing zone is provided which allows repeated fastening and unfastening of the tape tabs for inspection of the diaper. The three-piece TLZ is located at the front waist portion of the diaper. A center TLZ piece is positioned between and overlaps or underlaps the edges of the two outer TLZ pieces. The center TLZ piece has release characteristics different from that of the outer two pieces such that the tape tabs do not adhere securely to the center TLZ piece. This arrangement ensures correct alignment of the tape tabs on the outer TLZ surfaces.

25 Claims, 2 Drawing Sheets

THREE-PIECE TAPE LANDING ZONE FOR DIAPERS

This application claims the benefit of U.S. Provisional Application No. 60/048,185, filed May 30, 1997.

BACKGROUND OF THE INVENTION

1. Technical Field of the Invention

This invention relates to the field of the absorbent garments in general, and more particularly to a fastening system for absorbent garments with cloth-like nonwoven outer layers.

2. Description of the Prior Art

Disposable absorbent garments are well known in the art. Such garments typically include a moisture-impervious backing sheet, an absorbent pad, and a liner sheet that contacts the body of a person wearing the garment. In addition, elasticized regions are provided around the edges of the garment for securing it about the waist and legs of a wearer. Diapers typically further comprise opposed front and rear waist portions defining a waist opening, a crotch portion disposed therebetween, and a pair of elastically contractible leg openings along the side edges of the crotch portion. Disposable diapers having elasticized margins for placement about the legs of a wearer are disclosed in U.S. Pat. No. 4,050,462 and U.S. Pat. No. 5,092,861. An absorbent article having elasticized side margins and waist band margins is shown in U.S. Pat. No. 4,300,562.

Despite previous advancements in the field of absorbent garments, persons skilled in the art continue their efforts to produce more comfortable garments which are better able to contain urinary and fecal excretions. For instance, problems with prior diaper designs include leakage of urinary or fecal material from the garment. Prolonged contact of liquid or semi-solid excreta with the skin of the wearer is also a continuing problem in the art. The problem of leaking excreta may be further compounded by ineffective securing devices which hold the diaper around the child's waist.

Diapers may be secured around the body of the wearer by any of several known fastening systems. One such fastening system involves the use of adhesive tape tabs to secure the garment around the body of the wearer. The adhesive tape tabs are typically affixed to the rear waist portion of the backsheet. Corresponding tape landing zones (TLZ) are typically affixed to the front waist portion of the backsheet. The tape tabs adhere to the TLZ to secure the diaper or absorbent garment around the body of the wearer.

TLZs are typically affixed to the upper front waist portion of the backsheet of a diaper to provide a surface for secure fastening and reinforcement. TLZ surfaces allow the fastening tape tabs to be adjusted and refastened without tearing or otherwise damaging the backsheet. This feature is particularly convenient for inspecting the a contents of a diaper for waste. If no waste is found, the tape tabs may be refastened and use of the unsoiled diaper resumed.

Single-piece TLZs are known such as disclosed, for example, in U.S. Pat. Nos. 5,024,672 and 5,236,429, which are hereby incorporated by reference. In these prior art designs, the TLZ extends substantially across the entire upper front waist portion of the diaper. The fastening tape tabs adhere anywhere along the surface of the single TLZ strip. Consequently, the tape tabs might not be properly positioned along the TLZ strip, resulting in a poor fit.

Two-piece TLZs are also known. In this construction, two TLZ pieces form landing strips on the diaper where fastening tape tabs are attached. The backsheet of the diaper occupies the space between the respective pieces of the two-piece TLZ. Two-piece TLZ strips improve the fit of the diaper by reducing improper attachment of tape tabs to the TLZ. Two-piece TLZ strips also reduce the amount of material used in manufacturing the TLZ for a diaper and, thus, incrementally reduce the costs associated therewith.

In practice however, fastening tape tabs sometimes attach to the diaper backsheet in the space between the respective TLZ pieces. In such cases, removal of the tape tabs (for checking the contents of the diaper, readjusting or refastening) either tears the backsheet in this area or tears the TLZ piece(s) from the backsheet. Attempts to increase the tear strength or bond strength of the nonwoven backsheet laminate or the bond between the TLZ piece(s) and the nonwoven backsheet are either not economically practical or have not resolved this problem. This problem is exacerbated when the backsheet is fabricated from a cloth-like nonwoven material. These and other disadvantages of the prior art are sought to be overcome by the present invention.

SUMMARY OF THE INVENTION

It is an object of this invention to provide a three-piece TLZ in which the center TLZ piece has different release characteristics than the two outer TLZ pieces.

It is another object of this invention to provide a three-piece TLZ which may be used with cloth-like nonwoven backsheets in diapers.

It is another object of the invention to facilitate correct alignment of the adhesive tape tabs on a three-piece TLZ.

It is yet another object of the invention to provide a TLZ on which tape tabs may be repeatedly adjusted without tearing the backsheet of a diaper.

It is yet another object of the preferred embodiments to provide an absorbent garment comprising:

front and rear waist portions cooperating to form a waist opening;

a crotch region formed between said front and rear waist portions;

a pair of leg openings on opposed sides of the crotch region;

a permeable topsheet, a substantially impermeable backsheet, and an absorbent core positioned between said topsheet and said backsheet;

leg elastics extending at least through the crotch region and positioned between said topsheet and backsheet;

tape tabs attached to said backsheet at opposite sides of said rear waist portion; and a three-piece tape landing zone positioned on said backsheet adjacent said front waist portion, said three-piece tape landing zone comprising:

a central piece of plastic film substantially centrally secured to said backsheet at said front waist portion, said central piece of plastic film having two side edges; and two outer pieces of plastic film secured to said backsheet at respective sides of said first piece of plastic film; wherein said central piece of plastic film has different release characteristics than the two outer pieces of plastic film.

These and other objects of the invention are achieved by a three-piece TLZ comprising two outer TLZ pieces, which serve as fastening or landing zones for the tape tabs, and a third TLZ piece which has material and adhesive properties and characteristics different from those of the outer two TLZ pieces. The third or center TLZ piece is positioned between and overlaps the outer two TLZ pieces. Alternatively, the third or center TLZ piece is positioned between and underlaps the outer two TLZ pieces. In yet another preferred embodiment, the side edges of the third or center TLZ piece substantially align with respective edges of the outer TLZ pieces without underlap or overlap. The third piece thus prevents the tape tabs from attaching to the portion of the nonwoven backsheet located between the outer two TLZ pieces. The adhesive tape tabs can adhere securely to the outer two TLZ pieces, and can be repeatedly fastened and unfastened thereto. The third piece, having different release characteristics, prevents the adhesive tape tabs from securely fastening on its surface. Therefore, in order to achieve proper fastening, the tape tabs must be placed on the outer two TLZ pieces. The tape tabs are thus aligned correctly on the diaper, which in turn facilitates a better overall fit of the diaper.

In addition to the foregoing objects, the invention is further directed to a method of manufacturing a disposable absorbent garment including a three-piece TLZ. The three-piece TLZ is positioned on the upper front edge of the diaper during the manufacturing process and serves as fastening or landing zones for the tape tabs when the garment is worn. During manufacture, in the event that the third or center TLZ is positioned between and overlaps the outer two TLZ pieces, the outer TLZ pieces are first applied to the diaper backsheet, and then the center TLZ piece is applied to the diaper backsheet to overlap the corresponding inner edges of the outer two TLZ pieces. Alternatively, in the event that the third or center TLZ piece is positioned to underlap the outer two TLZ pieces, the inner TLZ piece is first applied to the front outer portion of the diaper backsheet, and then the outer two TLZ pieces are applied to the diaper backsheet to overlap corresponding end edges of the center TLZ pieces.

Other objects, features and advantages of the invention will become apparent by reference to the accompanying drawing and the following detailed description.

DETAILED DESCRIPTION OF THE PREFERRED EMBODIMENT

Figure 1:
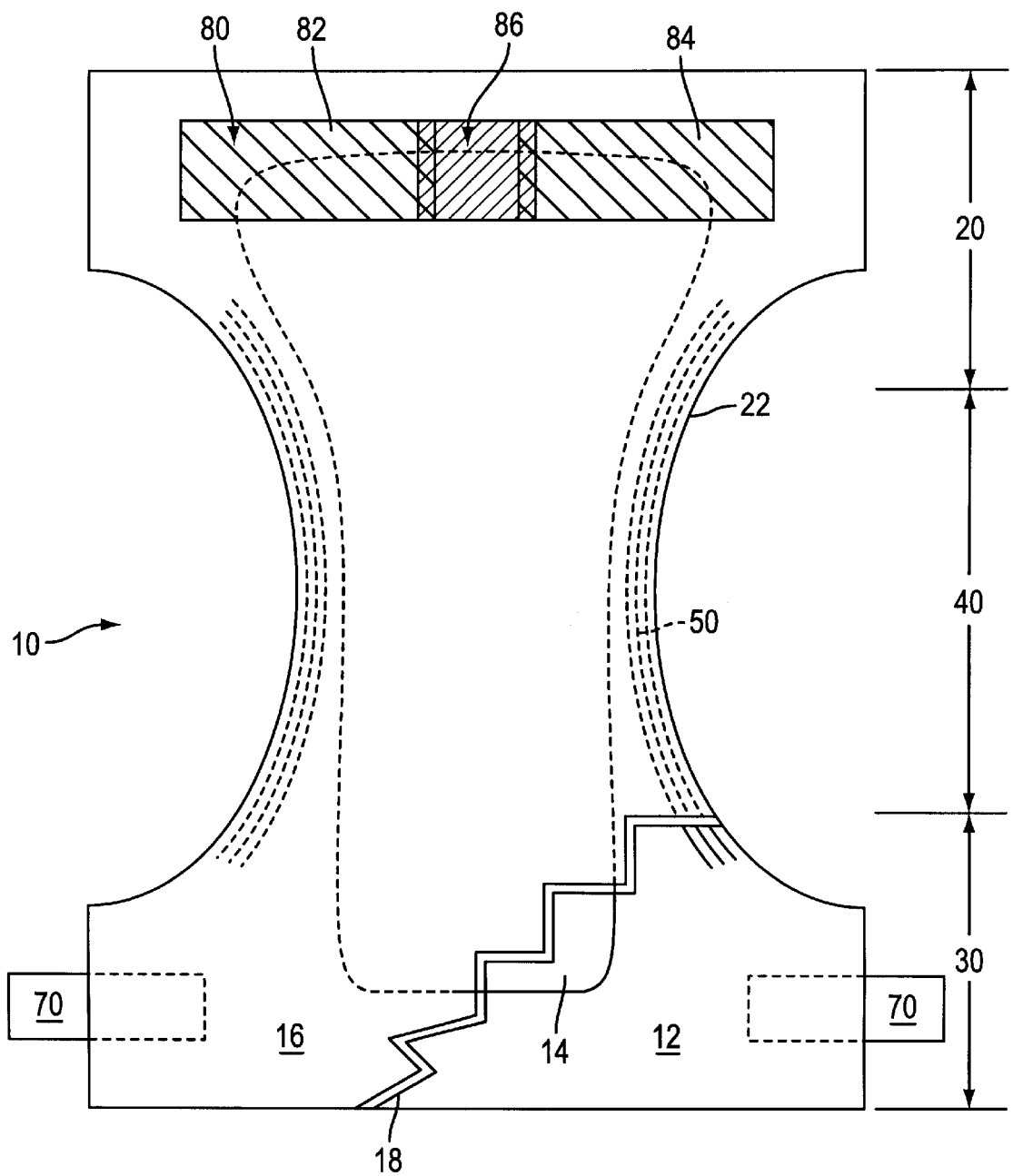
FIG. 1 shows a partially cut-away plan view of a diaper with a three-piece TLZ in accordance with the preferred embodiment of the present invention.

While the present invention is susceptible of embodiment in various forms, there is shown in the drawing and will hereinafter be described presently preferred embodiments, with the understanding that the present disclosure is to be considered as an exemplification of the invention, and is not intended to limit the invention to specific embodiment illustrated.

With reference to FIG. 1, a diaper having a three-piece TLZ in accordance with the preferred embodiment of the present invention is shown. Diaper 10 comprises opposed front and rear waist portions 20, 30. When the garment is applied to a wearer, front and rear waist portions 20, 30 cooperate to form a waist opening. A crotch region 40 is formed between front and rear waist portions 20, 30. A pair of leg elastics 50 extend substantially along the entire length of crotch region 40, and are positioned adjacent leg openings 22. While leg elastics 50 are illustrated as substantially following the profile of leg openings 22, leg elastics 50 may alternatively extend along substantially parallel attachment lines on opposite sides of the longitudinal centerline CL of the absorbent article 10. Diaper 10 further comprises a top sheet 12, an absorbent core 14, and an impermeable nonwoven cloth-like backsheet 16.

Absorbent core 14 is encased by topsheet 12 and backsheet 16. Absorbent core 14 may additionally be encased within tissue layer or layers 18 which, among other things, are designed to enhance the liquid take-up characteristics of the diaper 10 by wicking remote fluids to the area of absorbent core 14. Absorbent core 14 may be fabricated from any number of known absorbent materials, including wood pulp fibers and may optionally include a super-absorbent polymeric material known in the art. Absorbent core 14 may have a substantially hourglass shape. Alternatively, core 14 also may have a substantially rectangular shape. The absorbent core or pad is generally located in at least a perineal region of the article, but may extend more extensively throughout the diaper toward the waist elastics, which are generally applied to the respective edges of the front and rear waist portions between topsheet 12 and backsheet 16. As mentioned, super-absorbent particulate matter may optionally be used in absorbent core 14 in combination with wood pulp or absorbent fibers to produce a core permeated with super-absorbent particles, thereby enhancing its absorptive properties.

Backsheet 16 is preferably made from a nonwoven, moisture impervious material which is soft, cloth-like, and easily conformable to the body of the wearer. Alternatively, backsheet 16 may be fabricated from a nonwoven material that is laminated to a liquid impermeable polymeric film that is otherwise treated to render it impermeable, as is known in the art. Suitable nonwoven materials include spunlaced, spunbonded, meltblown and thermally bonded nonwoven fabrics comprising polyester, polypropylene, or polyethylene fibers. Alternatively, the moisture impervious backsheet 16 may be made from a thin thermoplastic material such as a polymer film. For example, the backsheet can be composed of a thin polyolefin film, such as polypropylene or polyethylene. In yet other embodiments, the backsheet can be composed of a liquid-impermeable micro-porous polyethylene film or a nonwoven spun bonded layer that has been completely or partially coated with a polymer film to provide a sufficient level of liquid impermeability in selected regions of the backsheet. Still further yet, and most preferably, backsheet 16 is fabricated from a material, which although liquid impermeably, exhibits breathability characteristics to permit air to flow therethrough.

Topsheet 12 is typically moisture pervious and may comprise a composite material having different degrees of moisture permeability. Examples of suitable topsheet materials are liquid permeable, substantially hydrophobic fibrous materials, such as a spun bonded web composed of synthetic polymer fibers. Alternatively, topsheet 12 may be a melt-blown web or a bonded-carded web of synthetic polymer fibers. Suitable synthetic polymers include polyethylene, polypropylene and polyesters. A particularly suitable material for topsheet 12 is a spun-bond polypropylene material having a basis weight of about 0.6 ounces per square yard. However, one skilled in the art of absorbent garment manufacture will realize that a wide variety of materials may be used to form backsheet 16, topsheet 12 and absorbent core 14. This invention is intended to encompass all such materials, and is not limited to the specific materials that are discussed herein.

More particularly, topsheet 12 preferably comprises a three component topsheet assembly positioned on top of the absorbent core 14, as disclosed, for example, in U.S. Pat. No. 5,275,590 to Huffman et al., which is hereby incorporated by reference. The three component assembly includes a central liquid permeable portion which generally overlies the absorbent panel, and a pair of side marginal portions joined to respective opposite side edges of the central portion.

As will be appreciated, a wide variety of materials may be employed for fabrication of the composite topsheet assembly. Nonwoven fabric materials are presently preferred, with the side marginal portions preferably comprising nonwoven materials exhibiting a relatively high degree of hydrophobicity. One suitable material for the side marginal portions is spunbond meltblown spunbond (SMS) nonwoven fabric having a basis weight in the range of about 0.3–0.8 ounces per square yard and a bond area in the range of about 7%–20%, with a basis weight of about 0.4–0.6 ounces per square yard and an 18% bond area being particularly preferred. When untreated, this material exhibits the desired degree of hydrophobicity. One commercially available material of this type is available from Polybond, Inc., of Waynesboro, Va., under the product designation DURO-SOFT 00680. Another commercially available material of this type is available from Veratec, a division of International Paper, Inc., of Walpole, Mass., under the product designation of EVERSPUN 83308.

The central portion of the composite topsheet assembly may also comprise a spunbond polypropylene nonwoven fabric having a basis weight and bond area as described above for the side marginal portions. While the central portion of the absorbent garment embodying the present invention can be selected to exhibit relatively high or relatively low liquid impermeability, it is presently preferred that the central portion be selected to exhibit significantly greater hydrophilicity, and thus greater liquid permeability, than the side portions. To this end, spunbonded polypropylene nonwoven materials such as described above are ordinarily treated with a surfactant to achieve the desired hydrophilicity. One commercially available material of this type is available from Polybond, Inc., of Waynesboro, Va., under the product designation DUROSOFT 5000. Alternatively, a hydrophobic fabric having apertures to permit liquid passage therethrough may be employed.

The diaper of the preferred embodiment may optionally be provided with a pair of inboard leg gathers (ILG's). The ILG's are typically positioned inboard of the leg openings 22 on opposite sides of the longitudinal centerline CL of the diaper. The ILG's may be fabricated from a hydrophobic material which is breathable to allow vapor to pass therethrough. Further, the ILG's are suitably elasticized along the length thereof to cause the distal ends thereof to rise above the surface of the topsheet and thereby from a barrier to the lateral flow of excreta. The manufacture and application of ILG's are well known to those skilled in the art and are not discussed in detail here.

Alternatively, rather than providing the absorbent garment with a pair of inboard ILG's, the absorbent garment may be provided instead with a unitary standing leg gather as disclosed, for example, in co-pending U.S. patent application Ser. No. 08/853,761, filed on May 9, 1997, assigned to the assignee of the present application, and which is hereby incorporated by reference. More specifically, the unitary standing leg gather may be formed from a portion of the topsheet which encloses one or more elastic elements extending from the front waist section to the rear waist section and positioned on opposite sides of the longitudinal center line of the absorbent article. The unitary standing leg gather advantageously combines the functional features of traditional leg elastics and inboard leg cuffs as disclosed, for example, in U.S. Pat. No. 5,246,431 to Minetola et al. Consequently, the unitary standing leg gather advantageously results in material savings without a corresponding sacrifice in performance.

Diaper 10 further preferably includes a pair of adhesive tape tabs 70 and a three-piece TLZ 80. Adhesive tape tabs 70 are secured to the rear waist portion 30 on the backsheet 16. The three-piece TLZ 80 is disposed at the front waist portion 20 on the backsheet 16.

The three-piece TLZ preferably comprises two outer pieces 82, 84 and a center piece 86. Outer pieces 82, 84 are fabricated from a material having properties suitable for allowing resealable securement of adhesive tape tabs 70 thereto. Outer pieces 82, 84 may be made from polyethylene, polypropylene, polyester or blends thereof or any other essentially inelastic material as described in U.S. Pat. No. 5,024,672, which is hereby incorporated by reference.

The center or third piece 86 of TLZ 80 has different release characteristics than outer TLZ pieces 82, 84. The release characteristics of center third piece 86 are such that fastening tape tabs 70 do not securely attach to center piece 86. Thus, in order to achieve adequate fastening, tape tabs 70 must be positioned on outer TLZ pieces 82, 84. Correct positioning and a proper fit of the diaper is thus improved.

All of the tape landing zone pieces 82, 84, 86 are preferably directly affixed to nonwoven backsheet 16. When tape tabs 70 are peeled from outer TLZs 82, 84, the TLZ pieces 82, 84 neither appreciably stretch nor rupture. This allows repeated fastening and refastening of the tape tabs 70 on the TLZ surface without damaging the garment.

Figure 2:
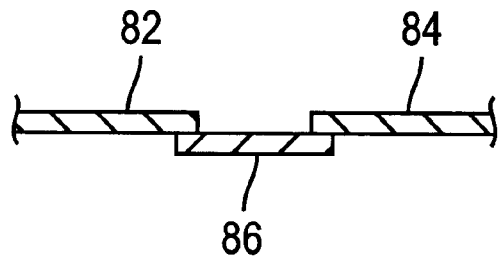
FIG. 2 is a partial cross-sectional view illustrating the three piece TLZ in which the outer TLZ pieces overlap the central TLZ pieces.
Figure 3:
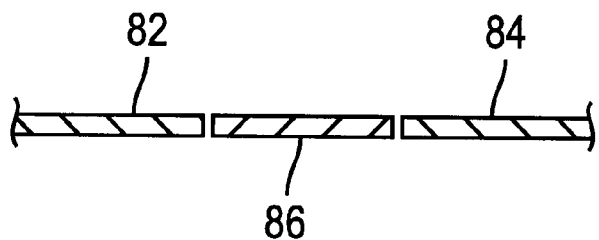
FIG. 3 is a partial cross-sectional view of the TLZ according to a second preferred embodiment in which the side edges of the outer TLZ pieces are aligned with the side edges of the central TLZ piece.
Figure 4:
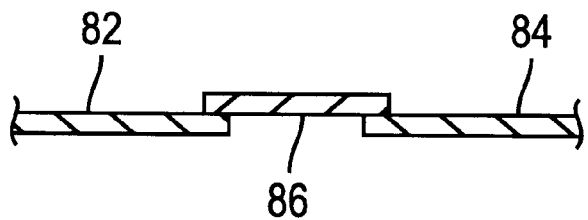
FIG. 4 is a partial cross-sectional view of the TLZ according to a third preferred embodiment in which the outer TLZ pieces underlap the side edges of the central TLZ piece.

As illustrated in FIG. 4, the third or center TLZ 86 is disposed between and preferably overlays the edges of the two outer TLZ pieces 82, 84. Center TLZ piece 86 prevents the fastening tape tabs 70 from inadvertently attaching to and tearing the nonwoven backsheet 16 of the diaper in the area between outer TLZ pieces 82, 84. TLZ piece 86 also prevents outer TLZ pieces 82, 84 from being pulled off the diaper when the tape tabs 70 are removed. Alternatively, as illustrated in FIG. 2, the third or center TLZ 86 is positioned between and underlaps the outer two TLZ pieces 82, 84. Still further yet, in another alternative embodiment illustrated in FIG. 3, the side edges of the third or center TLZ piece 86 substantially align with respective side edges of the outer TLZ pieces 82, 84 without any underlap or overlap.

More specifically, with respect to the adhesive release characteristics of the TLZs, outer TLZs 82, 84 preferably release when tape tabs 70 are peeled at an angle of about 180° with about an average peak of 300–800 grams of force and an average trace peel of about 300–600 grams of force, more preferably with about an average peak of 400–700 grams of force and an average trace peel of about 300–500 grams of force, most preferably with an average peak of about 500–600 grams of force and an average trace peel of about 400–500 grams of force. The center TLZ 86, on the other hand, preferably releases when tape tabs 70 are peeled at an angle of about 180° with an average trace peel of about preferably 5–40 grams of force, more preferably about 5–30 grams of force, and most preferably about 10–20 grams of force. This is to be contrasted with the 160–200 grams of average trace peel strength required to remove the release tapes at an angle of 180°, which cover the fastening tape tabs 70 during storage.

Outer TLZs 82, 84 are preferably formed from biaxially oriented polypropylene (BOPP). The BOPP may be purchased from 3-M under product name K-3098, for example. Center TLZ 86 is preferably fabricated from stock material obtained from 3-M under the product name KN-1453.

The absorbent garment may be manufactured in accordance with methods generally known in the art. However, according to an additional advantageous aspect of this invention, the three-piece TLZ may be positioned on the absorbent garment along the upper front outer edge of the backsheet during the manufacturing process. In the event that the third or center TLZ piece overlaps the outer two TLZ pieces, the outer TLZ pieces are first applied to the diaper backsheet, and then the center TLZ piece is applied to the diaper backsheet to overlap the corresponding inner edges of the outer two TLZ pieces. Alternatively, in the event that the third or center TLZ piece is positioned to underlap the outer two TLZ pieces, the inner TLZ piece is first applied to the front outer portion of the diaper backsheet, and then the outer two TLZ pieces are applied to the diaper backsheet to overlap corresponding end edges of the center TLZ piece.

In addition to individually applying each of the associated components of the three-piece tape landing zone to the front waist region of the backsheet, in an alternative embodiment the three-piece TLZ may be manufactured off-line so that it is preformed as a unitary strip when applied to the backsheet.

While the invention has been described in connection with the preferred embodiment, it will be understood by those skilled in the art that other variations and modifications of the preferred embodiment described above can be made without departing from the spirit and scope of the invention.

I claim:

1. An absorbent garment comprising:
   front and rear waist portions cooperating to form a waist opening;
   a crotch region formed between said front and rear waist portions;
   a pair of leg openings on opposed sides of the crotch region;
   a permeable topsheet, a substantially impermeable backsheet, and an absorbent core positioned between said topsheet and said backsheet;
   leg elastics extending at least through the crotch region and positioned between said topsheet and backsheet;
   tape tabs attached to said backsheet at opposite sides of said rear waist portion; and
   a three-piece tape landing zone positioned on said backsheet adjacent said front waist portion, said three-piece tape landing zone comprising:
      a central piece of plastic film substantially centrally secured to said backsheet adjacent said front waist portion, said central piece of plastic film having two side edges; and
      two outer pieces of plastic film secured to said backsheet at respective sides of said central piece of plastic film; wherein
      said central piece of plastic film has different release characteristics than the two outer pieces of plastic film.

2. The absorbent garment according to claim 1, wherein said two outer pieces of plastic film have edges which overlap said respective side edges of said central piece of plastic film.

3. The absorbent garment according to claim 1, wherein said two outer pieces of plastic film have edges which underlap said respective side edges of said central piece of plastic film.

4. The absorbent garment according to claim 1, wherein said two outer pieces of plastic film are selected from the group consisting essentially of polyethylene, polypropylene, polyester and blends thereof.

5. The absorbent garment according to claim 1, wherein said two outer pieces of plastic film are formed from substantially inelastic materials.

6. The absorbent garment according to claim 1, wherein said two outer pieces of plastic film have inner edges which are aligned with respective side edges of said central piece of plastic film.

7. The absorbent garment according to claim 1, wherein said two outer pieces of plastic film release said tape tabs when said tape tabs are peeled at an angle of about 180° with an average peak of about 300–800 grams of force and an average trace peel of about 300–600 grams of force.

8. The absorbent garment according to claim 1, wherein said two outer pieces of plastic film release said tape tabs when said tape tabs are peeled at an angle of about 180° with an average peak of about 400–700 grams of force and an average trace peel of about 300–500 grains of force.

9. The absorbent garment according to claim 1, wherein said two outer pieces of plastic film release said tape tabs when said tape tabs are peeled at an angle of about 180° with an average peak of about 500–600 grams of force and an average trace peel of about 400–500 grams of force.

10. The absorbent garment according to claim 1, wherein said central piece of plastic film releases said tape tabs when said tape tabs are peeled at an angle of about 180° with an average trace peel of about 5–40 grams of force.

11. The absorbent garment according to claim 1, wherein said central piece of plastic film releases said tape tabs when said tape tabs are peeled at an angle of about 180° with an average trace peel of about 5–30 grams of force.

12. The absorbent garment according to claim 1, wherein said central piece of plastic film releases said tape tabs when said tape tabs are peeled at an angle of about 180° with an average trace peel of about 10–20 grams of force.

13. The absorbent garment according to claim 1, wherein said two outer pieces of plastic film comprise biaxially oriented polypropylene.

14. The absorbent garment according to claim 1, wherein said backsheet comprises a non-woven composite, and said two outer pieces of plastic film and said central piece of plastic film are attached to said non-woven composite.

15. An absorbent garment comprising:
   front and rear waist portions cooperating to form a waist opening;
   a crotch region formed between said front and rear waist portions;
   a pair of leg openings on opposed sides of the crotch region;
   a permeable topsheet;
   a substantially impermeable backsheet;
   an absorbent core positioned between said topsheet and said backsheet;

a pair of stand-up elasticized leg gathers having a distal edge and a proximal edge and positioned inboard of said leg openings on opposite sides of a longitudinal center line of the absorbent garment, said leg gathers comprising a hydrophobic non-woven material and having elastic threads adjacent said distal edge, said elastic threads causing said leg gathers to rise above said topsheet;

tape tabs attached to said backsheet at opposite sides of said rear waist portion; and a three-piece tape landing zone positioned on said backsheet adjacent said front waist portion, said three-piece tape landing zone comprising:

a central piece of plastic film substantially centrally secured to said backsheet adjacent said front waist portion, said central piece of plastic film having two side edges; and two outer pieces of plastic film secured to said backsheet at respective sides of said central piece of plastic film; wherein said central piece of plastic film has different release characteristics than the two outer pieces of plastic film.

16. The absorbent garment according to claim 15, said topsheet having a basis weight of about 0.6 ounces per square yard, said topsheet comprising a central liquid permeable portion and a pair of side marginal portions joined to respective opposite side edges of said central portion, said side marginal portions comprising spun-bond, melt-blown, spunbond (SMS) non-woven material having a basis weight in the range of about 0.3–0.8 ounces per square yard, said central portion of said topsheet comprising a spun-bond polypropylene non-woven fabric.

17. The absorbent garment according to claim 15, said backsheet comprising a nonwoven material selected from the group consisting essentially of spun-laced, spunbonded, and melt-blown fibers.

18. The absorbent garment according to claim 17, wherein said fibers are selected from the group consisting essentially of polyester, polypropylene, and polyethylene fibers.

19. The absorbent garment according to claim 15, further comprising leg elastics positioned adjacent respective leg openings between said topsheet and said backsheet.

20. An absorbent garment comprising:

front and rear waist portions cooperating to form a waist opening;

a crotch region formed between said front and rear waist portions;

a pair of leg openings on opposed sides of the crotch region;

a permeable topsheet, a substantially impermeable backsheet, and an absorbent core positioned between said topsheet and said backsheet;

leg elastics extending at least through the crotch region and positioned between said topsheet and backsheet;

tape tabs attached to said backsheet at opposite sides of said rear waist portion; and a three-piece tape landing zone positioned on said backsheet adjacent said front waist portion, said three-piece tape landing zone comprising:

a central piece of plastic film substantially centrally secured to said backsheet adjacent said front waist portion, said central piece of plastic film having two side edges, said central piece of plastic film releases when said tape tabs are peeled at an angle of about 180° with an average trace peel of about 5–40 grams of force; and two outer pieces of plastic film secured to said backsheet at respective sides of said central piece of plastic film, said two outer pieces of plastic film release when said tape tabs are peeled at an angle of about 180° with about an average peak of 300–800 grams of force and an average trace peel of about 300–600 grams of force.

21. The absorbent garment according to claim 20, wherein said two outer pieces of plastic film have edges which overlap said respective side edges of said central piece of plastic film.

22. The absorbent garment according to claim 20, wherein said two outer pieces of plastic film have edges which underlap said respective side edges of said central piece of plastic film.

23. The absorbent garment according to claim 20, wherein said two outer pieces of plastic film have inner edges which are aligned with respective side edges of said central piece of plastic film.

24. The absorbent garment according to claim 20, wherein said two outer pieces of plastic film are selected from the group consisting essentially of polyethylene, polypropylene, polyester and blends thereof.

25. The absorbent garment according to claim 20, wherein said two outer pieces of plastic film comprise biaxially oriented polypropylene.

* * * * *